(12) United States Patent
Fletcher

(10) Patent No.: US 9,198,990 B2
(45) Date of Patent: Dec. 1, 2015

(54) DISINFECTING DEVICE

(71) Applicants: W. J. Hays, Warren, OH (US); Doris M. Hays, Warren, OH (US)

(72) Inventor: Richard Glen Fletcher, Salem, OH (US)

( * ) Notice: Subject to any disclaimer, the term of this patent is extended or adjusted under 35 U.S.C. 154(b) by 0 days.

(21) Appl. No.: 14/066,199

(22) Filed: Oct. 29, 2013

(65) Prior Publication Data

US 2014/0158910 A1 Jun. 12, 2014

Related U.S. Application Data

(60) Provisional application No. 61/719,686, filed on Oct. 29, 2012.

(51) Int. Cl.
*A61L 2/10* (2006.01)

(52) U.S. Cl.
CPC .......................................... *A61L 2/10* (2013.01)

(58) Field of Classification Search
USPC .............................. 250/455.11; 422/24, 186.3
See application file for complete search history.

(56) References Cited

U.S. PATENT DOCUMENTS

| | | | |
|---|---|---|---|
| 3,503,703 A | | 3/1970 | McDonald |
| 4,112,485 A | * | 9/1978 | Sutter ............................ 362/369 |
| 4,877,964 A | * | 10/1989 | Tanaka et al. ............ 250/455.11 |
| 5,160,699 A | | 11/1992 | Siegal |
| 6,028,315 A | | 2/2000 | Bailey et al. |
| 6,753,536 B2 | * | 6/2004 | Humphreys et al. ..... 250/455.11 |
| 6,811,748 B2 | | 11/2004 | Ettlinger et al. |
| 7,304,312 B2 | | 12/2007 | Hopaluk et al. |
| 7,612,492 B2 | | 11/2009 | Lestician |
| 8,193,515 B2 | | 6/2012 | Kreitenberg |
| 2002/0182104 A1 | | 12/2002 | Carman et al. |
| 2004/0120850 A1 | * | 6/2004 | Kaiser ............................. 422/22 |
| 2005/0201910 A1 | | 9/2005 | Shou et al. |
| 2006/0186358 A1 | | 8/2006 | Couvillion |
| 2006/0277107 A1 | | 12/2006 | Beal et al. |
| 2007/0274879 A1 | * | 11/2007 | Millikin ..................... 422/186.3 |
| 2010/0044582 A1 | * | 2/2010 | Cooper et al. ........... 250/455.11 |

OTHER PUBLICATIONS

Sep. 28, 2010; NewTec's Unique Shopping Cart Sanitizer Installed at Giant Eagle; Kevin Howell.
Sep. 30, 2010; The SanitiZer Rids Shopping Carts of Germs and Bacteria; Ruth Lang.
2011; The SanitiZer by NewTec Corporation.

* cited by examiner

*Primary Examiner* — Kiet T Nguyen
(74) *Attorney, Agent, or Firm* — Zollinger & Burleson Ltd.

(57) ABSTRACT

A sanitizing system uses ultraviolet light within a housing having an interior chamber. When items such as shopping carts or wheel chairs are moved into and out of the interior chamber, a cover is moved to reduce the light shining out of the housing. The cover is coordinated with the door of the housing to limit light shining on the users of the system. In another configuration, a switch is used to turn off the light source to reduce the light shining out of the housing when items such as shopping carts or wheel chairs are moved into and out of the interior chamber. In both of the systems described above, the sanitizing system may use a single sanitizing source such as a UV light source or a combination of sanitizing systems such as a UV light source in combination with a source of disinfecting plasma.

18 Claims, 6 Drawing Sheets

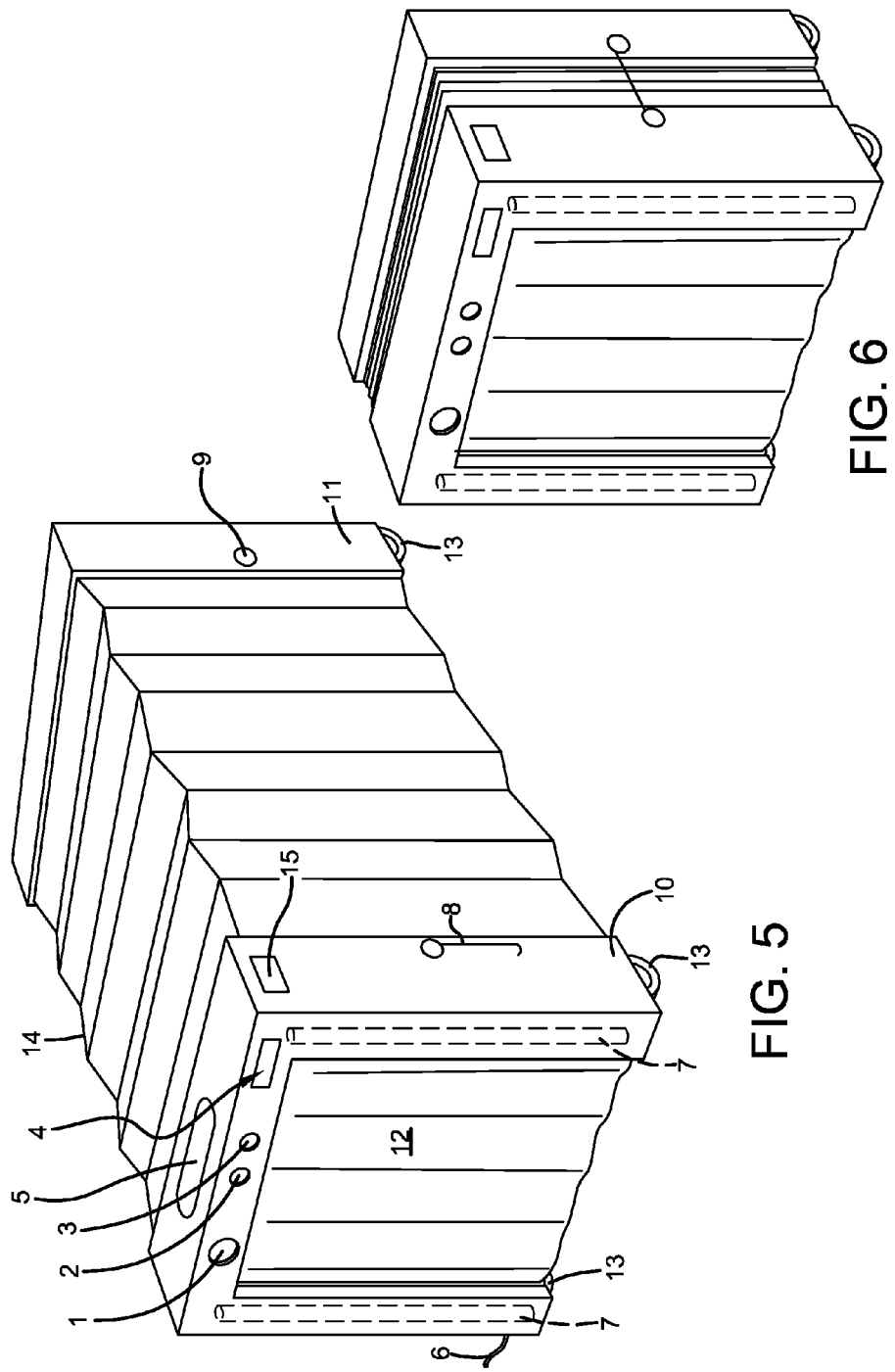

DISINFECTING DEVICE

CROSS REFERENCE TO RELATED APPLICATIONS

This application claims the benefit of United States Provisional Patent Application 61/719,686 filed Oct. 29, 2012; the disclosures of which are incorporated herein by reference.

BACKGROUND OF THE DISCLOSURE

1. Technical Field

The disclosure generally relates to machines used to disinfect items and, more particularly, to disinfecting enclosures used to disinfect items placed within or passed through the enclosure.

2. Background Information

There is an increasing concern by the users of shopping carts about the level of germs found on the carts. Such germs can be deposited on the cart handle from the previous user's hands, the infant seat from a leaking diaper, or can develop in the cart basket or in the infant seat from leaking food packaging. Each retail and grocery store provides shopping carts used by hundreds of customers and their children each day. Leaky meat packages and leaky diapers are fairly common. Pathogens remain and multiply after the leaks dry. Some studies have shown that publicly-used shopping carts have more germs or pathogens than public restrooms. Numerous studies found *E-Coli* on more than 50% of carts tested. Exposure to raw meat & poultry products, by riding in shopping carts, increases risk of salmonella and *e-coli* infections in children younger than three. Existing solutions to these problems include disinfecting wipes provided by grocery stores, disinfecting sprays, washing with soap and water, and providing disposable covers for the infant seat. Some shoppers carry their own covers after becoming aware of the issue.

The issue of disinfecting large equipment is also found with the users of wheelchairs, patient beds, tables, carts, and other shared medical equipment. Wheelchairs used in healthcare facilities and airports are used by multiple people and can collect germs from a variety of sources. Patient beds and beds used with medical testing equipment also can collect germs and need to be disinfected. Such disinfection should lead to lower infection rates and thus better patient experiences at the healthcare facility.

Some of the germs of concern include Methicillin-sensitive *Staphylococcus Aureus* (MSSA), Methicillin-resistant *Staphylococcus Aureus* (MRSA), *Escherichia coli* (*E. coli*), *Clostridium difficile* (C-Diff), A *Streptococcus* (Strep), and Scabies mite. Widespread use of antibiotics has caused some pathogens to "adapt," becoming more resistant to treatment and more aggressive in nature.

The number of nursing homes has exploded in recent years and often residents share equipment. Beds, gurneys, wheelchairs, bedside tables, blood pressure cuffs, stethoscopes and more are all used in the care of multiple patients in nursing homes and hospitals. People can acquire a pathogen-related illness while they are in a health care facility and being treated for something totally unrelated to the acquired illness. One study has shown that health-care acquired illnesses (HAIs) in the United States account for more than 140 deaths each day.

Airports provide wheelchair service to move travelers to and from departure and arrival gates. Pathogens travel with passengers and contaminate the wheelchairs they use. Customers and sky-caps are regularly exposed to these health hazards.

In each case, disinfecting shared items with traditional disinfecting methods takes time and is often a "hit and miss" process. Grocery carts and airport wheel chairs may go as long as six months between thorough cleanings. Those cleanings may or may not involve proper use of disinfectants. Equipment in health care settings may be disinfected more frequently, but rarely more than once a day and generally not that often.

SUMMARY OF THE DISCLOSURE

In one configuration, the disclosure provides a sanitizing system that uses ultraviolet light within a housing having an interior chamber. When items such as shopping carts or wheel chairs are moved into and out of the interior chamber, a cover is moved to reduce the light shining out of the housing. The cover is coordinated with the door of the housing to limit light shining on the users of the system.

In another configuration, the disclosure provides a sanitizing system that uses ultraviolet light within a housing having an interior chamber. When items such as shopping carts or wheel chairs are moved into and out of the interior chamber, a switch is used to turn off the light source to reduce the light shining out of the housing.

In both of the systems described above, the sanitizing system may use a single sanitizing source such as a UV light source or a combination of sanitizing systems such as a UV light source in combination with a source of disinfecting plasma.

In any of the systems described above, the sanitizing system can include a highly reflective surface disposed on all or portions of the inside of the housing to reflect the UV-C light waves and increase the efficiency of the disinfecting system. A mirror type surface enhances the reach of the UV light rays on the item disposed in the housing. It is also believed imperfections or irregularities further increase the effectiveness of the UV-C disinfecting device. One exemplary material that may be used is a polished aluminum tread or diamond plate. Another example is a metalized polymer material such as metalized polyethylene or metalized corrugated material. Both of these materials may be formed to have surface irregularities.

BRIEF DESCRIPTIONS OF THE DRAWINGS

FIG. 5 is a perspective view of a third configuration of the system.

FIG. 6 is a perspective view of the third configuration in a collapsed configuration.

DETAILED DESCRIPTION OF THE DISCLOSURE

Figure 1:
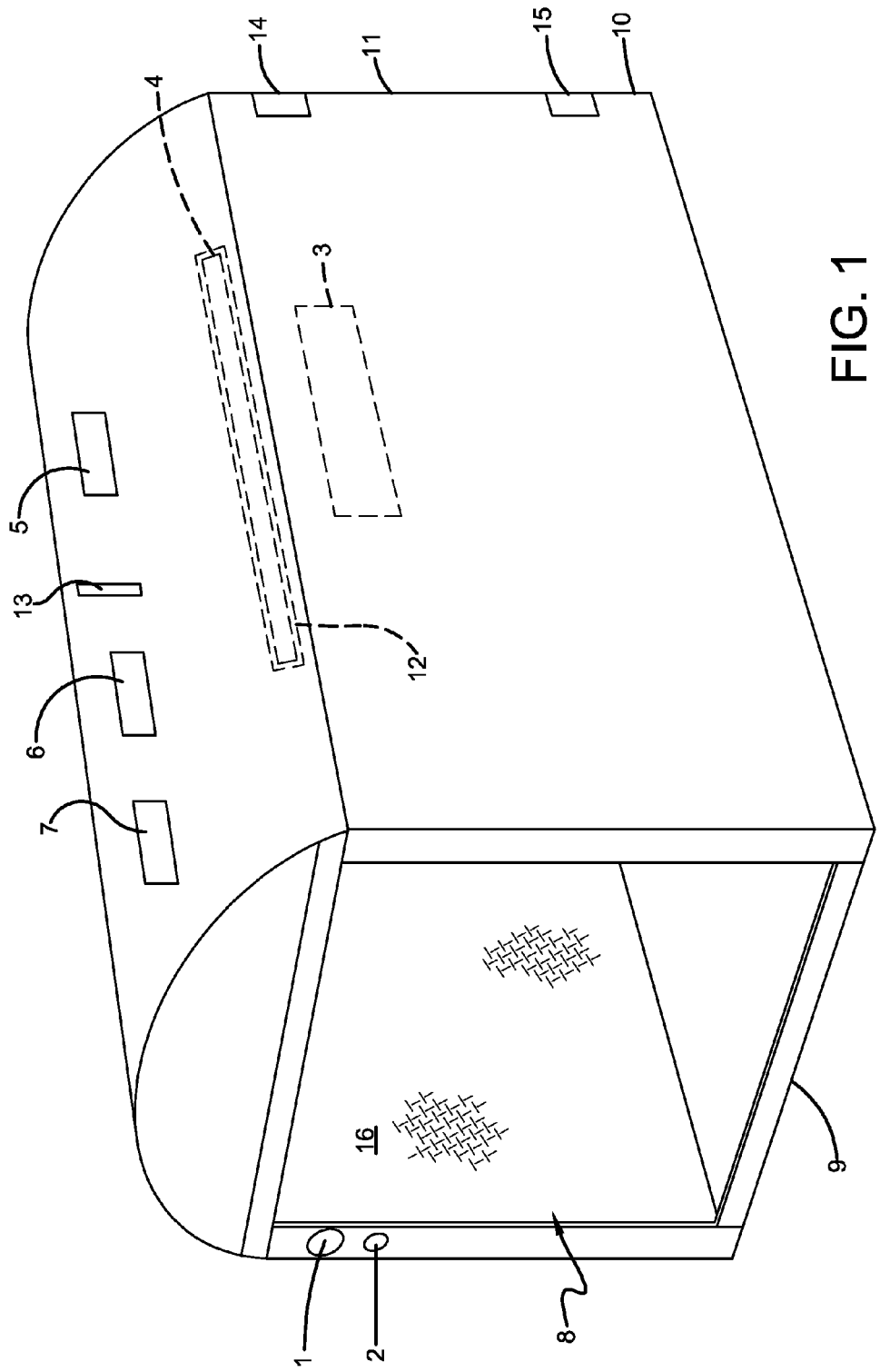
FIG. 1 is a perspective view of one configuration of the system.

The devices described herein generally include first and second disinfecting systems that, when used in combination and in the manners described herein, have been found to effectively disinfect various items of equipment in a relatively fast and effective manner.

The first disinfecting system is an ionization system such as a photocatalytic ionization (PCI) process. Different systems are available to implement this process. One such system is a photohydroionization (PHI) cell. The PHI cell is used to reduce viruses and bacteria in various areas. The PHI cell uses an ionization technology, radiant catalytic ionization (RCI), that transforms oxygen and moisture from the air into active, germ-killing agents. The photohydroionization technology uses safe low-level ozone, super oxide ions, hydroperoxides, hydroxides, ozonide ions and UV light to remove particles, microbes, gases and odors from the atmosphere. The PHI cell operates on 110 volts of AC current. The PHI Cell creates an advanced oxidation process that includes hydro peroxides, super oxide ions and hydroxide ions. All are friendly oxidizers that revert back to hydrogen and oxygen after eradicating or killing pollutants. One example of a PHI cell that may be used is the Photo Catalytic Ionization (PHI) unit sold by GreenTech Environmental in Gray, Tenn. Dimensions of cell 2.25"W×10.5"L×1.25"D 115 Volt AC power 3 year life.

The second disinfecting system is a germicidal ultraviolet light (UV-C) used for ultraviolet disinfection. The UV-C light inactivates microorganisms by disrupting their cellular membranes and by damaging their DNA or RNA. The ultraviolet light initiates a reaction between two molecules of thymine, one of the bases that make up DNA. Ultraviolet light at 254 nm wavelength (germicidal UV or UV-C) causes adjacent thymine molecules on DNA to dimerize. The thymine dimer is very stable. When enough of these defects accumulates on a microorganism DNA its replication is inhibited, results in effective UV disinfection by rendering the microorganisms harmless. The germicidal ultra-violet (UV-C) light is in the region of maximum germicidal effectiveness and is highly lethal to virus, bacteria, protozoa and mold.

Each disinfecting system is effective by itself, but both are relatively slow to disinfect. In the desired applications, the device must disinfect quickly. In combination, the disinfecting process is intensified and accelerated. What might take an hour or more to achieve individually, the combined first and second disinfecting systems are believed to achieve in significantly less time especially when used in combination with reflective surfaces or reflective surfaces having a plurality of surface irregularities.

The non-ozone producing, UV-C bulbs remain 100% effective for 7000 on/off cycles or two years, whichever occurs first. For this reason, the unit is always on, but only requires the energy of a 75 watt bulb. After two years the effectiveness of the bulb begins to decline. In humans, UV-C is absorbed in the outer dead layers of the epidermis. Accidental overexposure to UV-C can cause corneal burns, commonly termed welders' flash, and snow blindness, a severe sunburn to the face. While UV-C injury usually clears up in a day or two, it can be painful. The device configurations described herein are thus designed to keep light from the UV-C bulbs out of the field of vision of the user and those passing by the device. Skin exposure is limited to the time required to insert and remove the item(s) to be disinfected.

Activated oxygen ions are very effective at destroying a wide range of harmful microbials; i.e., virus, bacteria, mold and fungus.

These first and second combined disinfecting systems may be used with each of the configurations described below. In addition, a highly reflective surface may be used on all or portions of the inside of any of the systems described below to reflect the UV-C light waves and increase the efficiency of the disinfecting system. A mirror type surface enhances UV light rays which, in turn greatly increases the effectiveness of the UV-C device on pathogens and viruses. It is also believed imperfections or irregularities further increase the effectiveness of the UV-C disinfecting device. One exemplary material that may be used is a polished aluminum tread or diamond plate. Another example is a metalized polymer material such as metalized polyethylene or metalized corrugated material. Both of these materials may be formed to have surface irregularities.

The UV-C bulbs in each of the devices may be encapsulated for safety.

In all of the configurations described below, a system may be provided to turn off the lights when the door or doors to the units are open. Alternatively, a system for covering the lights may be provided so that a user is no directly exposed to the lights when a door is open. These covers may be opaque plates that move over the lights to block the lights from view even while the lights stay on. This configuration allows the unit to function quickly while limiting direct exposure to the lights by users.

In each of the configurations described below, the units may be provided with floors to limit discoloration of the surface on which they are supported.

The units may be provided with sensors that automatically turn on and turn off the devices when a door is opened and closed or when an item is disposed above the threshold. A timer may be used to indicate when an item is disinfected. The timer may be used to turn off (or cover the lights) such that the user knows that the item being disinfected has been in the unit long enough to be disinfected. A counter may be used with each configuration to allow the owner of the device to track usage and perform maintenance.

The different configurations may be provided with wheels to make them mobile. The different configurations may be provided in different sizes and—as shown in the third configuration—may be adjustable in size to allow for mobility in an elevator and through smaller doorways.

Figures 2A, 2B:
FIGS. 2A-2C depict different items that may be sanitized or disinfected in the system.
Figure 2C:

A first configuration of the disinfecting device that combines the first and second disinfecting systems is depicted in FIG. 1. FIG. 1 is a perspective view of a first configuration of the disinfecting machine with reference numeral 1 indicating a start button, reference numeral 2 indicating an on light (activity), reference numeral 3 indicating a PCI cell, reference numeral 4 indicating a UVC light, reference numeral 5 indicating a ballast, reference numeral 6 indicating a junc. box electrical, reference numeral 7 indicating a timer (8 seconds), reference numeral 8 indicating an opening enter, reference numeral 9 indicating a threshold—plastic enter, reference numeral 10 indicating a threshold—plastic exit, reference numeral 11 indicating an opening exit, reference numeral 12 indicating a light cover when not in use, reference numeral 13 indicating a unit to cover and expose UV light, reference numeral 14 indicating a safety switch (on/off), and reference numeral 15 indicating a power cord. The unit depicted in FIG. 1 is a pass through unit. Reference numeral 16 indicates a reflective material (such as aluminum treadplate). FIGS. 2A-2C depict a variety of items that can be disinfected in the device of FIG. 1. The configuration of FIG. 1 is a pass-through unit with an entrance 8 and an exit 11. Thresholds 9 and 10 define the entrance and exit for wheeled vehicles that are passed through the device. Sensors or switches may be used to activate the device. A switch 1 is shown as being used to activate the device. The floor surface under the device may be covered with a device floor to prevent discoloration of the floor surface under the device. A plurality of interior surfaces of the device may be covered with a reflective material such as the aluminum tread material described above. In this configuration, UV-C lights 4 are disposed lengthwise along the length of the pass through unit and each light is covered with a movable cover 12 that selectively exposed the light when the device is activated. A control unit 13 is provided to move cover 12 back and forth between covered and exposed conditions. The opening and exit may be covered with a door or curtain to limit the light exiting the unit. The floor of the device may be provided with a conveyor to move items through the unit. Each light 4 may be surrounded by a shatterproof protective shield to limit clean-up if light 4 should break and to limit accidental impacts to light 4.

Figure 3:
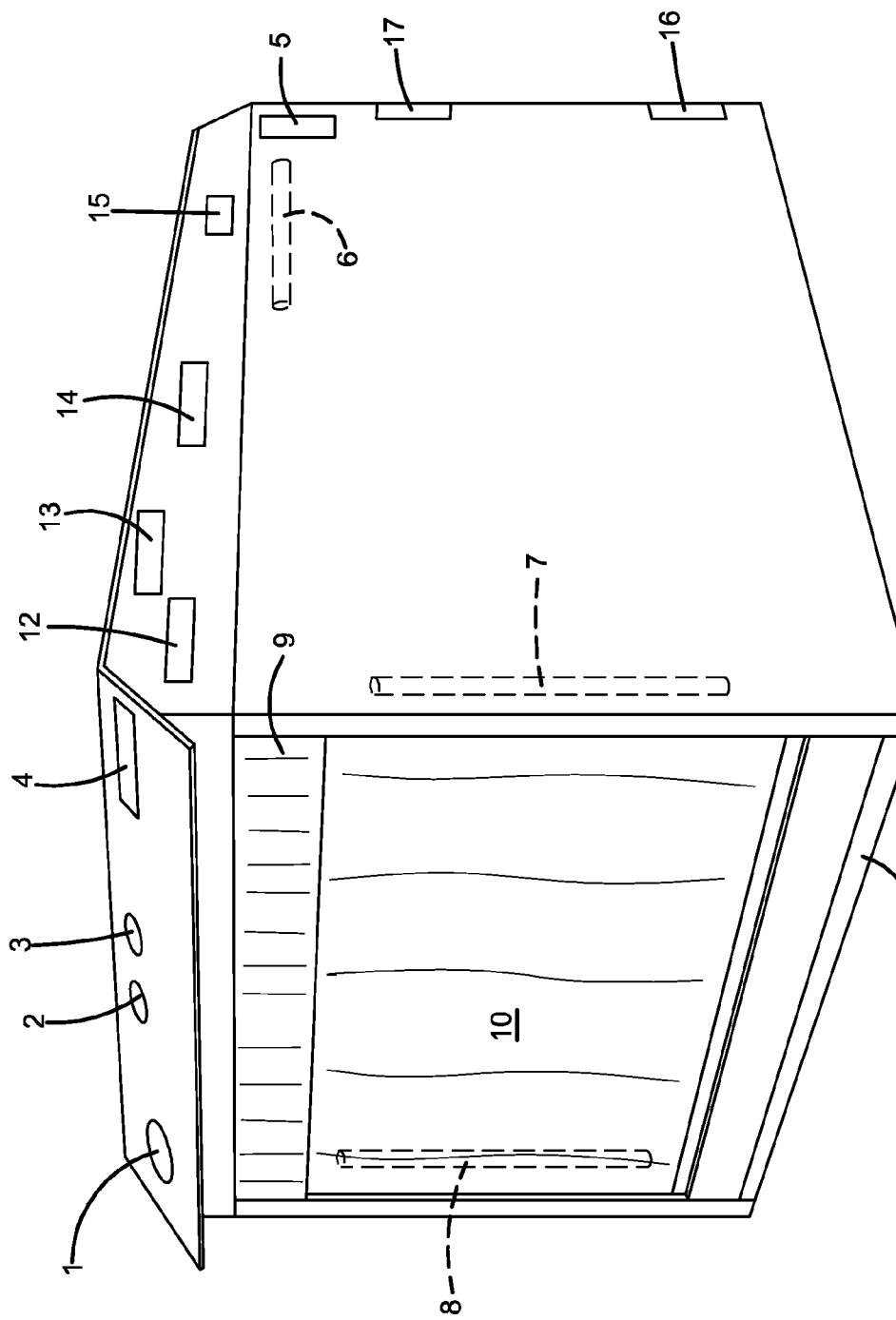
FIG. 3 is a perspective view of a second configuration of the system.
Figure 4A:
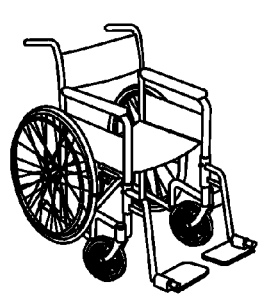
FIGS. 4A-4G depict different items that may be sanitized or disinfected in the system.
Figure 4B:
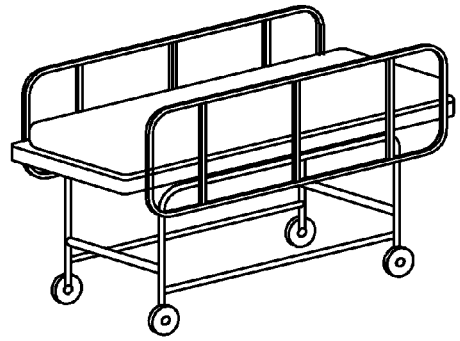
Figure 4C:
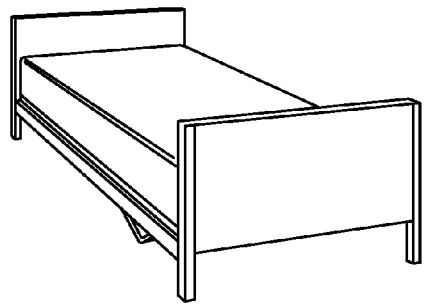
Figure 4D:
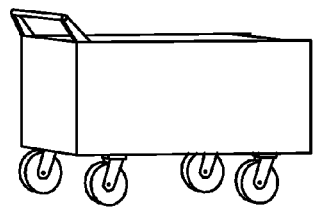
Figure 4E:
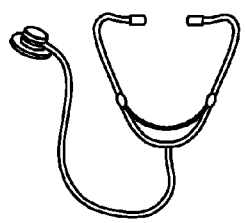
Figure 4F:
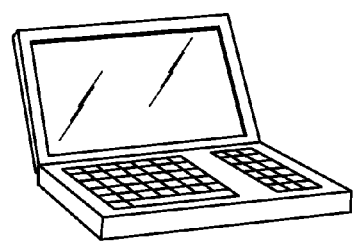
Figure 4G:
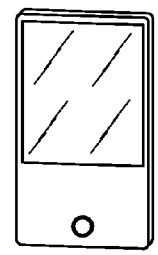

A second configuration of the disinfecting device that combines the first and second disinfecting systems is depicted in FIG. 3. FIG. 3 is a perspective view of a second configuration of the disinfecting machine with reference numeral 1 indicating a start button, reference numeral 2 indicating a working light, reference numeral 3 indicating a ready light, reference numeral 4 indicating a counter, reference numeral 5 indicating a PCI Cell, reference numeral 6 indicating a twenty-four inch UVC, reference numeral 7 indicating a thirty-six inch UVC disposed on one side of the door 10, reference numeral 8 indicating a thirty six inch UVC disposed on the other side of the door 10, reference numeral 9 indicating a UV shield, reference numeral 10 indicating a door, reference numeral 11 indicating a threshold, reference numeral 12 indicating a timer, reference numeral 13 indicating a first ballast, reference numeral 14 indicating a power-junction box, reference numeral 15 indicating a second ballast, reference numeral 16 indicating a power inlet, and reference numeral 17 indicating a safety switch (on/off). The unit of FIG. 3 may be provided with or without door 10. The interior (roof, back, and both sides) are high polished tread plate. The exterior may be polymer or metal. FIGS. 4A-4G depict a variety of items that can be disinfected in the device of FIG. 3. This configuration of the device includes a plurality of UV-C lights with a pair disposed inside the device on the sides of the entrance. These may be tucked behind the edge portions of the front wall to limit direct views of the lights from those users disposed outside the device. The third light is disposed in the top rear of the device which also limits direct views from those users located outside the device. A UV shield 9 may be provided to further limit exposure or sight lines. The door 10 may be a solid hinged door or a pair of solid hinged doors. A curtain style door 10 also may be used. The door 10 may be automatic and controlled with switch 1 where the lights are turned off or covered before the door is opened and then the lights are turned back on when the door is closed. A timer may be used to control the opening and closing or may be used to simply activate a ready light that indicates when the item disposed within the unit may be removed.

A third configuration of the disinfecting device that combines the first and second disinfecting systems is depicted in FIGS. 5-6. FIGS. 5-6 show perspective views of a third configuration of the disinfecting machine with reference numeral 1 indicating an activation switch or mechanism to activate timer, reference numeral 2 indicating a "Ready to Use" indicator—illuminated when power on and off when timer activated, reference numeral 3 indicating an "In Use" indicator—illuminated for duration of timer activation, reference numeral 4 indicating a counter—increments once for each timer activation, reference numeral 5 indicating one (or more) Photo Catalytic Ionization (PCI) unit(s) (also known as Radiant Catalytic Ionization—RCI), reference numeral 6 indicating an AC power cord—provides power (alternate embodiment could be DC power source with recharging unit), reference numeral 7 indicating one (or more) germicidal UV light(s)—UV-C—primarily 254 nm wavelength generation, reference numeral 8 indicating a latching mechanism to secure for transport—one on each side (cord/knob or hook/latch), reference numeral 9 indicating a mating part for latching mechanism 8, reference numeral 10 indicating the control end housing (houses controls, indicators, UV-C light(s), PCI unit(s) and closure), reference numeral 11 indicating a threshold, reference numeral 12 indicating a timer, reference numeral 13 indicating a first ballast, reference numeral 14 indicating a power-junction box, reference numeral 15 indicating a second ballast, reference numeral 16 indicating a power inlet, and reference numeral 17 indicating a safety switch (on/off). This configuration is an expandable and collapsible unit that allows it to be easily transported (via the wheels) throughout a facility such as a medical facility or a nursing home to disinfect beds and other medical equipment. When used on a hospital bed, the unit may be wheeled into a room in a collapsed condition and then expanded over the bed and turned on. When finished, the unit is turned off and collapsed and then wheeled out of the room. The walls 14 can be accordion style with a flexible reflective material on the inside or a nested configuration wherein panels slide over each other. When used with wheel chairs, the unit may be set up at a convenient location and the chairs may be passed through the unit from one to four at a time to disinfect the chairs. Once finished, the unit may be collapsed for storage or wheeled to a different location for continued use.

Figure 7:
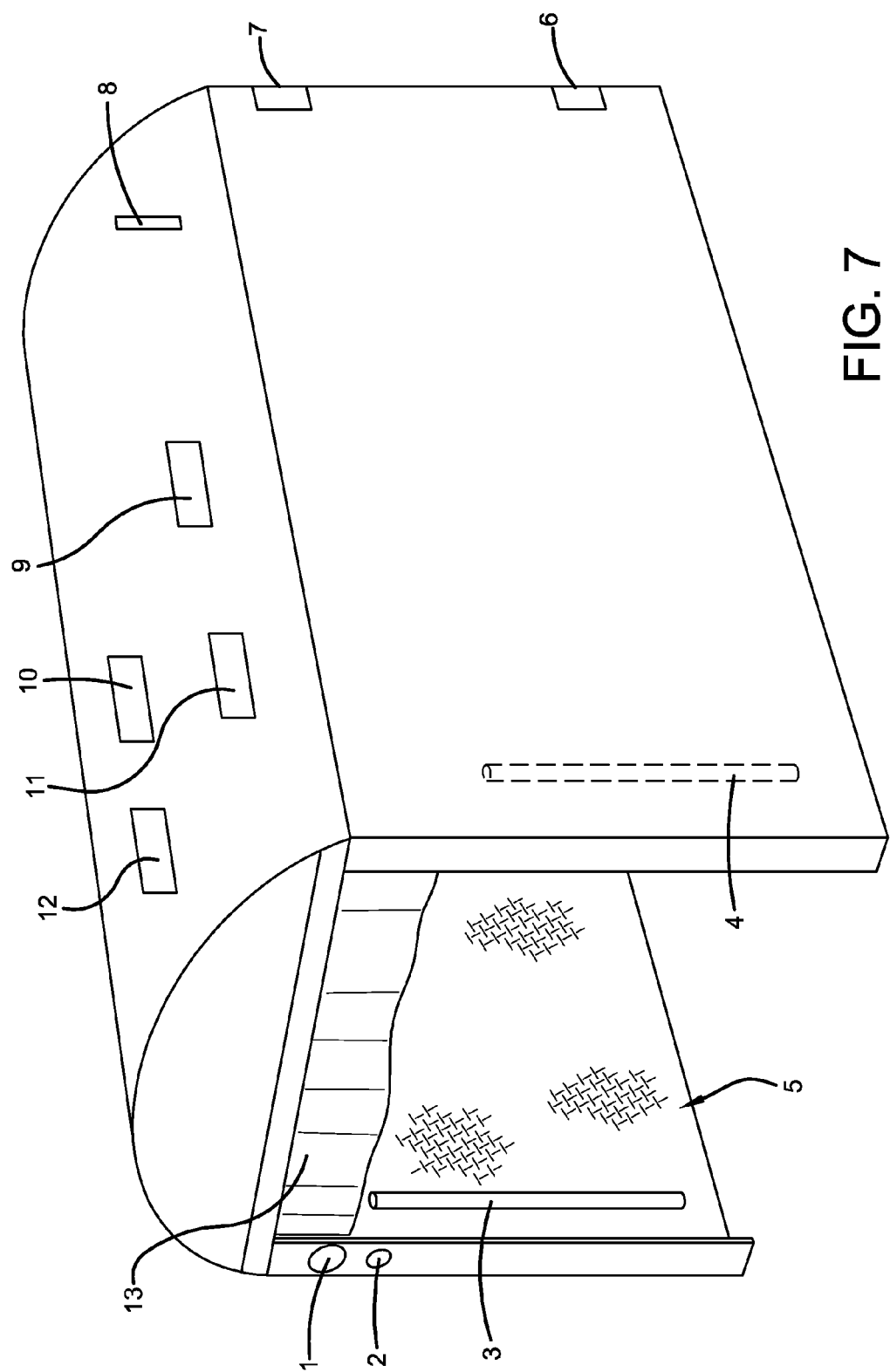
FIG. 7 is a perspective view of a fourth configuration of the system.

A fourth configuration of the disinfecting device that combines the first and second disinfecting systems is depicted in FIG. 7. FIG. 7 is a perspective view of a fourth configuration of the disinfecting machine reference numeral 1 indicating a start button, reference numeral 2 indicating an activity light, reference numeral 3 indicating a UVC bulb disposed on one side of the door opening, reference numeral 4 indicating a UVC bulb disposed on the other side of the door opening, reference numeral 5 indicating polished tread plate (right wall and left wall), reference numeral 6 indicating a power inlet, reference numeral 7 indicating an on/off switch, reference numeral 8 indicating a PCI cell, reference numeral 9 indicating a ballast, reference numeral 10 indicating a junc. box for wire connections, reference numeral 11 indicating a ballast for UVC, reference numeral 12 indicating a timer, and reference numeral 13 indicating a safety shield. This configuration is similar to the first configuration except for the closed rear wall of the device.

Exemplary Applications:
Airports

An exemplary disinfecting device for wheel chairs that significantly reduces the level of commonly occurring viruses and bacteria that can affect public health. Overall dimensions are nominally 57" high×42" wide×54" deep. The access opening is nominally 47" high×36" wide. It comes standard with a UV guard, weighs approximately 150 pounds and operates on standard 110 V current. Purchase, lease-purchase and financing options are available.

The skycap disinfects each wheelchair before each use. Not only does this protect the traveler, but it protects the skycap from acquired illnesses, as well.

Getting to the gate on time should be a mobility-challenged traveler's only concern.

Safely getting there with minimal exposure to health risks should be expected.

Travelers can rest assured each time they travel through an airport that cares enough to use this type of disinfecting device.

Shopping Carts

Another exemplary disinfecting device is used for shopping carts and significantly reduces the level of commonly occurring viruses and bacteria that can affect public health. Overall dimensions are nominally 66" high×42" wide×54" deep. It is a "pass thru" device with access openings nominally 56" high×36" wide. It comes standard with a UV guard at both ends, weighs approximately 140 pounds and operates on standard 110 V current. Purchase, lease-purchase and financing options are available. This device is used by each customer prior to placing a child or merchandise into the cart. Establishments that take the initiative to address health hazards are perceived as being a "cut above" their competition. Customers know that the store cares about them and their health safety. They shop in confidence, knowing that they can control the use of this state-of-the-art disinfecting device each time they shop.

Health Care Facility

Additional exemplary configurations are disinfecting devices that reduce the level of commonly occurring viruses and bacteria well below generally accepted standards. Both are available in one of two standard color schemes; i.e., tan/brown (earthtones) and light gray/charcoal. One configuration is used in medical equipment rental companies and on the patient floors of hospitals and nursing homes. Overall dimensions are nominally 66" high×42" wide×54" deep. Access opening is nominally 56" high×36" wide. It comes standard with a UV guard and slide-latch door and weighs approximately 160 pounds. Another configuration is used to disinfect gurneys on surgical floors and at emergency entrances of hospitals, as well as hospital beds. Overall dimensions are nominally 76" high×54" wide×104" deep. Access opening is nominally 66" high×48" wide. It comes standard with a UV guard and slide-latch door and weighs approximately 265 pounds.

Because these devices are conveniently located, easy to use and require 60 seconds or less to operate (unattended!), health care facilities can expect significant reduction in nosocomial illnesses related to surface-borne pathogens. This can be a huge benefit to patients and the financial bottom line of the facility. Purchase, lease-purchase and financing options are available.

In the foregoing description, certain terms have been used for brevity, clearness, and understanding. No unnecessary limitations are to be implied therefrom beyond the requirement of the prior art because such terms are used for descriptive purposes and are intended to be broadly construed. Moreover, the above description and attached illustrations are an example and the invention is not limited to the exact details shown or described. Throughout the description and claims of this specification the words "comprise" and "include" as well as variations of those words, such as "comprises," "includes," "comprising," and "including" are not intended to exclude additives, components, integers, or steps.

The invention claimed is:

1. A system for sanitizing an item; the system comprising:
    a housing defining an interior chamber; the housing having an opening that allows the item to be sanitized to be placed into the interior chamber of the housing;
    a first source of sanitizing UV light associated with the housing; the first source providing UV light to the interior chamber of the housing;
    a photohydroionization (PHI) cell used in cooperation with the UV light; and
    the housing having an interior surface; the interior surface being reflective and irregular surface.

2. The system of claim 1, wherein the sanitizing UV light is UV-C light.

3. The system of claim 1, wherein the reflective and irregular surface interior surface of the housing is a surface of a section of aluminum tread.

4. The system of claim 1, wherein the reflective and irregular surface interior surface of the housing is a surface of a section of diamond plate.

5. The system of claim 1, wherein the reflective and irregular surface interior surface of the housing is a surface of a section metalized polymer material.

6. The system of claim 1 wherein the reflective and irregular surface interior surface of the housing is a surface of a section metalized corrugated material.

7. The system of claim 1, wherein the first source of sanitizing UV light is encapsulated in a protective housing.

8. The system of claim 7, wherein the protective housing is shatter-proof.

9. The system of claim 1, further comprising a door having open and closed conditions; the open condition of the door allowing access to the interior chamber; the closed condition of the door limiting access to the interior chamber; and
    the UV light source being turned off when the door is in the open condition.

10. A system for sanitizing an item; the system comprising:
    a housing defining an interior chamber; the housing having an opening that allows the item to be sanitized to be placed into the interior chamber of the housing;
    a first source of sanitizing UV light associated with the housing; the first source providing UV light to the interior chamber of the housing;
    the housing having an interior surface; the interior surface being reflective and irregular surface;
    a door having open and closed conditions; the open condition of the door allowing access to the interior chamber; the closed condition of the door limiting access to the interior chamber; and
    a light cover that moves to a blocking position when the door is moved to the open condition; the blocking position of the light cover reducing the amount of UV light reaching the opening that defines access to the interior chamber.

11. The system of claim 10, wherein the sanitizing UV light is UV-C light.

12. The system of claim 10, wherein the reflective and irregular surface interior surface of the housing is a surface of a section of aluminum tread.

13. The system of claim 10, wherein the reflective and irregular surface interior surface of the housing is a surface of a section of diamond plate.

14. The system of claim 10, wherein the reflective and irregular surface interior surface of the housing is a surface of a section metalized polymer material.

15. The system of claim 10, wherein the reflective and irregular surface interior surface of the housing is a surface of a section metalized corrugated material.

16. The system of claim 10, wherein the first source of sanitizing UV light is encapsulated in a protective housing.

17. The system of claim 16, wherein the protective housing is shatter-proof.

18. The system of claim 10, further comprising a photohydroionization (PHI) cell used in cooperation with the UV light.

* * * * *